US00PP12484P2

(12) United States Plant Patent
Olesen et al.

(10) Patent No.: US PP12,484 P2
(45) Date of Patent: Mar. 26, 2002

(54) MINIATURE ROSE PLANT NAMED 'POULFIRY'

(76) Inventors: L. Pernille Olesen; Mogens N. Olesen, both of Hillerodvejen 49, Fredensborg (DK), DK-3480

( * ) Notice: Subject to any disclaimer, the term of this patent is extended or adjusted under 35 U.S.C. 154(b) by 0 days.

(21) Appl. No.: 09/277,237

(22) Filed: Mar. 26, 1999

(51) Int. Cl.[7] ..... A01H 5/00
(52) U.S. Cl. ..... Plt./119
(58) Field of Search ..... Plt./119, 116, 120

(56) References Cited

PUBLICATIONS

UPOV–ROM GTITM Computerbase 2000/06, Dec. 8, 2000, GTI Jouve Retrieval Software, citation for 'Poulfiry'.*

* cited by examiner

*Primary Examiner*—Bruce R. Campell
*Assistant Examiner*—June Hwu

(57) ABSTRACT

A new garden rose plant which has abundant, orange-red flowers and attractive foliage. This new and distinct variety has shown to be uniform and stable in the resulting generations from asexual propagation.

1 Drawing Sheet

SUMMARY OF THE INVENTION

The present invention constitutes a new a new and distinct variety of garden rose plant which originated from a controlled crossing between two unnamed seedlings (non-patented). The two parents were crossed and the resulting seeds were planted in a controlled environment. The new variety is named 'POULfiry'.

The new rose may be distinguished from its seed parent, an unnamed seedling, created by the same inventors, by the following combination of characteristics:

1. The seed parent has yellow blooms while 'POULfiry' has orange-red blooms;

The new variety may be distinguished from its pollen parent, an unnamed seedling, created by the same inventors, by the following combination of characteristics:

1. The pollen parent has a lighter color of orange flowers compared to 'POULfiry' which has orange-red flowers.

The objective of the hybridization of this rose variety for garden use was to create a new and distinct variety with unique qualities, such as:

1. Uniform and abundant flowers;
2. Vigorous, compact growth;
3. Continual bloom; and
4. Miniature foliage and flowers.

This combination of qualities is not present in previously available commercial cultivars of this type and distinguishes 'POULfiry' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULfiry' was selected in the spring, 1991 by the inventors as a single plant from the progeny of the aforementioned hybridization.

Asexual reproduction of 'POULfiry' by cuttings and traditional budding was first done by L. Pernille and Mogens N. Olesen in August 1991. This initial and other subsequent propagations conducted in controlled environments have demonstrated that the characteristics of 'POULfiry' are true to type and are transmitted from one generation to the next.

BRIEF DESCRIPTION OF THE DRAWING

The accompanying color illustration shows, as true as is reasonably possible to obtain in color photographs of this type, the typical characteristics of the buds, flowers, leaves, and stems of 'POULfiry'. Specifically illustrated in SHEET 1:

1. Stem showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULfiry', as observed in its outdoor growth in a field nursery in Jackson County, Oreg., on plants aged eighteen months. Observations were conducted during October, 1998. Color references are made using The Royal Horticultural Society (London, England) Colour Chart, 1995, except where common terms of color are used.

For a comparison, several physical characteristics of the rose variety 'POULrouge', a miniature rose variety from the same inventors described and illustrated in U.S. Plant Pat. No. 9,687 and issued on Nov. 12, 1996 are compared to 'POULfiry' in Chart 1.

CHART 1

| | 'POULfiry' | 'POULrouge' |
|---|---|---|
| Open bloom size. | 35–40 mm. | 40 mm. |
| Open bloom color, upper surface. | Red Group 40B–40C. | Red Group 40B. |
| Plant height. | 55–65 cm. | 40 cm. |

Parents:
*Seed parent.*—Unnamed seedling.
*Pollen parent.*—Unnamed seedling.
Classification:
*Botanical.*—*Rosa hybrida.*
*Commercial.*—Miniature.

FLOWER AND FLOWER BUD

Blooming habit: Continuous.
Flower bud:
*Size.*—Upon opening, 20 mm–24 mm in length from base of receptacle to end of bud.
*Bud form.*—Pointed ovoid to globular.
*Bud color.*—As sepals unfold, Red Group 45B. Red Group 41A–41B at ¼ opening.
*Sepals.*—Yellow-Green Group 143B. Moderated to strong foliaceous appendages with intonations of Greyed-Red Group 180A on lower surface. Upper surface is Green Group 137B. Surfaces of sepals are slightly pubescent. Stipitate glands are present on margins and thin white hairs are present on outer surface. Sepals are 15 to 20 mm long and 8 to 11 mm wide. The apex is subulate.
*Receptacle.*—Surface: Smooth, slightly pubescent. Shape: Urn-shaped. Size: Medium, 4 mm (h)×6 mm (w). Color: Green Group 137C with intonations of Greyed-Red Group 180A.
*Peduncle.*—Surface: Smooth, with a fine pubescence. Limited numbers of stipitate glands observed. Length: 25–30 mm average length. Color: Yellow-Green Group 144A to Yellow-Green Group 144B, with intonations of Greyed-Red Group 180A. Strength: Strong.
*Borne.*—2–6 buds per flowering stem.
Flower bloom:
*Fragrance.*—Light floral scent.
*Duration.*—The blooms have a duration on the plant of approximately 3 to 7 days. Petals fall cleanly away from plant.
*Size.*—Average flower diameter is 35–40 mm when open.
*Form.*—Shape of flower when viewed from the side: Upon opening, upper part: Convex. Upon opening, lower part: Flattened convex. Open flower, upper part: Flattened convex. Open flower, lower part: Flat.
*Petalage.*—Double, with 20–25 petals under normal conditions with 3–6 petaloids.
Color:
*Upon opening, petals.*—Outermost petals: Upper Surface: Basal zone Red Group 40A, middle zone is Red Group 40B, marginal zone Red Group 40C. Reverse Side: Marginal Zone Red Group 41C and middle to basal zone 41B. Innermost petals: Upper Surface: Red Group 40A. Reverse Side: Red Group 41A–42C.
*Upon opening, basal petal spot.*—Outermost petals: Outer Side: Yellow-Orange Group 22B. Inner Side: Yellow-Orange Group 22A–22B. Innermost petals: Outer Side: Yellow-Orange Group 22B. Inner Side: Yellow-Orange group 22A.
*After opening, petals.*—Outermost petals: Upper Surface: Red Group 40C. Reverse Side: Red Group 41C. Innermost petals: Upper Surface: Red Group 40B. Reverse Side: Red Group 41B.
*After opening, basal petal spot.*—Outer Side: Yellow-Orange Group 22B. Inner Side: Yellow-Orange Group 22A.
General tonality: On open flower Red Group 40B–40C. No change in the general tonality at the end of the 3rd day. Afterwards, general tonality is Red Group 40C–40D.
Petals:
*Petal reflex.*—Petals reflexed, outermost petals are double reflexed.
*Petal edge.*—Entire.
*Shape.*—Obovate.
*Petaloids.*—3 to 6. Petaloids are 5 to 10 mm long and 4 to 6 mm wide. Petaloid texture is smooth. Coloration is Red Group 40C.
*Thickness.*—Moderately thick.
*Arrangement.*—Imbricated.
Reproductive organs:
*Pollen.*—Color: Yellow-Orange Group 17C. Quantity: Average.
*Anthers.*—Size: Anthers are 3 to 5 mm long. Color: Immature anthers range from Yellow-Orange Group 21C to Greyed-Orange Group 168C. Mature anthers are Greyed-Orange Group 165B. Quantity: 25 to 30.
*Pistils.*—Size: 7 to 10 mm long. Quantity: 20 to 25 per inflorescence.
*Hips.*—None observed.
*Filaments.*—Color: Yellow-Orange Group 23A.
*Stigmas.*—Slightly superior in location to anthers.
*Styles.*—Color: Green-White Group 157A. Intonations: Immediate below stigma, intonations of Greyed-Red Group 179A.

PLANT

Plant growth: Moderately vigorous, compact, upright to bushy. When grown as a budded field grown plant on *Rosa multiflora* understock, the average height of the plant itself is 60–65 cm and the average width is 60 cm.
Stems:
*Color.*—Young wood: Yellow-Green Group 144B. Older wood: Yellow-Green Group 146C.
*Thorns.*—Incidence: 5 to 7 per 10 cm of stem length. Color: Immature thorns are Yellow-Green Group 145D. Mature thorns are Greyed-Orange Group 166C. Shape: Linear with downward curvature.
*Surface.*—Young wood: Smooth. Older wood: Smooth.
Plant foliage: Normal number of leaflets on leaves in middle of the stem: 5 leaflets.
*Leaf size.*—Small, 50–60 mm (l)×35–45 mm (w).
*Quantity.*—Average.
*Color.*—Upper Leaf Surface: Green Group 137A to Yellow-Green Group. Lower Leaf Surface: Yellow-Green Group 147C. Juvenile foliage: Green Group 137B. Anthocyanin: Location: Leaflets, rachis, petioles, stipules, thorns, stems, and peduncles. Color: Greyed-Purple Group 183B.
Plant leaves and leaflets:
*Stipules.*—Size: 8 mm–10 mm. Color: Yellow-Green Group 146B. Stipitate glands: On margins.
*Petiole.*—Length: 12 mm–15 mm. Color: Yellow-Green Group 146B with intonations of Greyed-Red Group 183B on upper surface. Underneath: Smooth. Margins: Stipitate glands present.
*Rachis.*—Color: Yellow-Green Group 146B with intonations of Greyed-Red Group 183B on upper surface. Underneath: Smooth. Margins: With stipitate glands.

*Leaflets.*—Edge: Serrated. Shape: Ovate. The leaflet's apex is acuminate. The leaflet's base is rounded. Arrangement: The leaflets are arranged in an odd-pinnate formation. Venation: The leaflets are veined in a reticulate pattern. Texture: Leaves are thick. Upper side of leaflet is glossy. Lower side of leaflet is matte.

Disease resistance: Average resistance to mildew, black spot, and under normal growing conditions in Jackson County, Oreg.

Winter hardiness: 'POULfiry' has been found to be resistant to damage from cold in USDA Zone 8 and USDA Zone 7.

We claim:

1. A new and distinct variety of rose plant of the miniature class, substantially as herein illustrated and described as a distinct and novel rose variety due to its abundant, orange-red flowers, vigorous but, dwarf growth, and extended period of bloom.

* * * * *

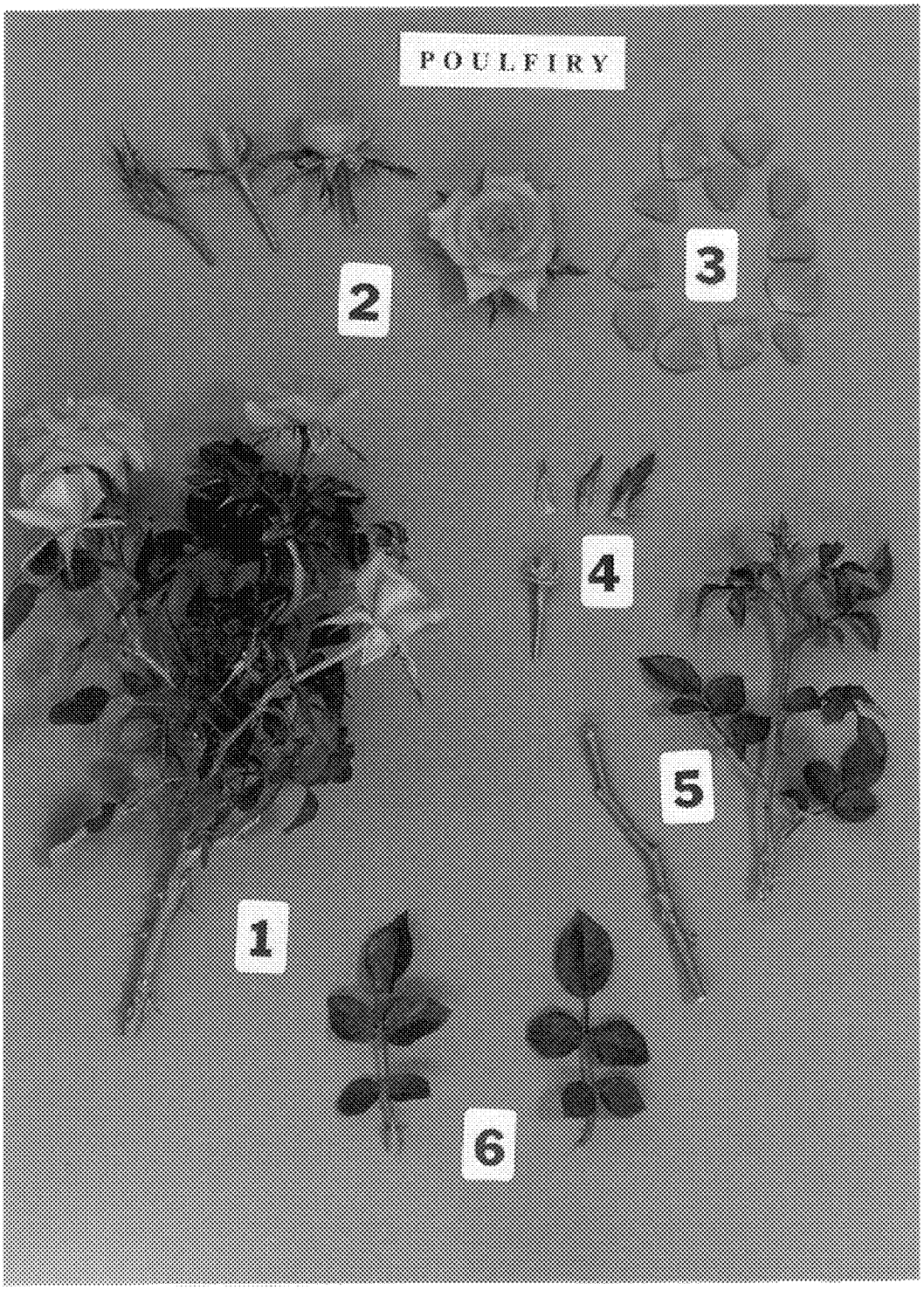
POULFIRY
2
3
4
5
1
6